(12) United States Patent
Thomas et al.

(10) Patent No.: US 6,494,841 B1
(45) Date of Patent: Dec. 17, 2002

(54) MEDICAL DIAGNOSTIC ULTRASOUND SYSTEM USING CONTRAST PULSE SEQUENCE IMAGING

(75) Inventors: Lewis Jones Thomas, Palo Alto, CA (US); Samuel H. Maslak, Woodside, CA (US); Patrick Phillips, Sunnyvale, CA (US); Gregory L. Holley, Mountain View, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/514,803

(22) Filed: Feb. 29, 2000

(51) Int. Cl.[7] .................................................. A61B 8/00
(52) U.S. Cl. ....................................... 600/447; 600/458
(58) Field of Search ................................ 600/443, 437, 600/447, 458

(56) References Cited

U.S. PATENT DOCUMENTS

| | | | | |
|---|---|---|---|---|
| 5,113,706 A | * | 5/1992 | Pittaro | 73/626 |
| 5,577,505 A | | 11/1996 | Brock-Fisher et al. | |
| 5,608,690 A | * | 3/1997 | Hossack et al. | 367/138 |
| 5,632,277 A | | 5/1997 | Chapman et al. | |
| 5,833,613 A | * | 11/1998 | Averkiou et al. | 600/440 |
| 5,833,615 A | | 11/1998 | Wu et al. | |
| 5,902,243 A | * | 5/1999 | Holley et al. | 600/443 |
| 5,951,478 A | | 9/1999 | Hwang et al. | |
| 6,080,107 A | * | 6/2000 | Poland | 600/458 |
| 6,095,980 A | * | 8/2000 | Burna et al. | 600/453 |
| 6,108,572 A | * | 8/2000 | Panda et al. | 600/407 |
| 6,319,203 B1 | * | 3/2001 | Averkiou | 600/443 |
| 6,340,348 B1 | * | 1/2002 | Krishnan et al. | 600/447 |
| 6,361,498 B1 | * | 3/2002 | Brock-Fisher | 600/458 |

OTHER PUBLICATIONS

Bruno Haider and Richard Y. Chiao, "Higher Order Non-linear Ultrasonic Imaging", 1999 IEEE Ultrasonic Symposium Proceedings.

* cited by examiner

*Primary Examiner*—Francis J. Jaworski

(57) ABSTRACT

A medical diagnostic ultrasound imaging method fires a sequence of pulses into a body and then receives, beamforms, weights and sums the resulting echo signals to suppress first order echoes. The sequence of pulses includes at least two pulses that differ in amplitude and phase. In one form, no two pulses of the sequence have the same amplitude and opposite phase. In another form, only linear echoes are suppressed. In a third form, second and third order echoes are preserved while linear echoes are suppressed.

52 Claims, 10 Drawing Sheets

MEDICAL DIAGNOSTIC ULTRASOUND SYSTEM USING CONTRAST PULSE SEQUENCE IMAGING

BACKGROUND

Contrast agents are useful for ultrasound imaging because their presence can preferentially enhance scattering from regions of tissue depending on disease state. Therefore, the important element of contrast agent detection is the sensitivity of the detection scheme to echoes from contrast agent relative to echoes from tissue. We refer to this sensitivity to contrast echoes versus tissue echoes as specificity.

SUMMARY

High specificity to contrast agents can be achieved in two ways: by exploiting the greater nonlinear response of contrast agents over tissue, particularly to low amplitude pulses, or by detecting modification (destruction, for example) of the contrast agent by an acoustic wave (the loss of correlation or LOC effect). (Tissue is not modified by the passage of an acoustic wave at diagnostic power levels.) This specification describes a technique called Contrast Pulse Sequence (or CPS) imaging that improves the specificity of contrast agent detection when the nonlinear response of the agent is used to distinguish contrast agent from tissue, maintains sensitivity to contrast agent when the LOC effect is used, and improves rejection of signals from moving tissue, which can corrupt the contrast agent signals.

DETAILED DESCRIPTION OF THE PREFERRED EMBODIMENTS

Figure 1:
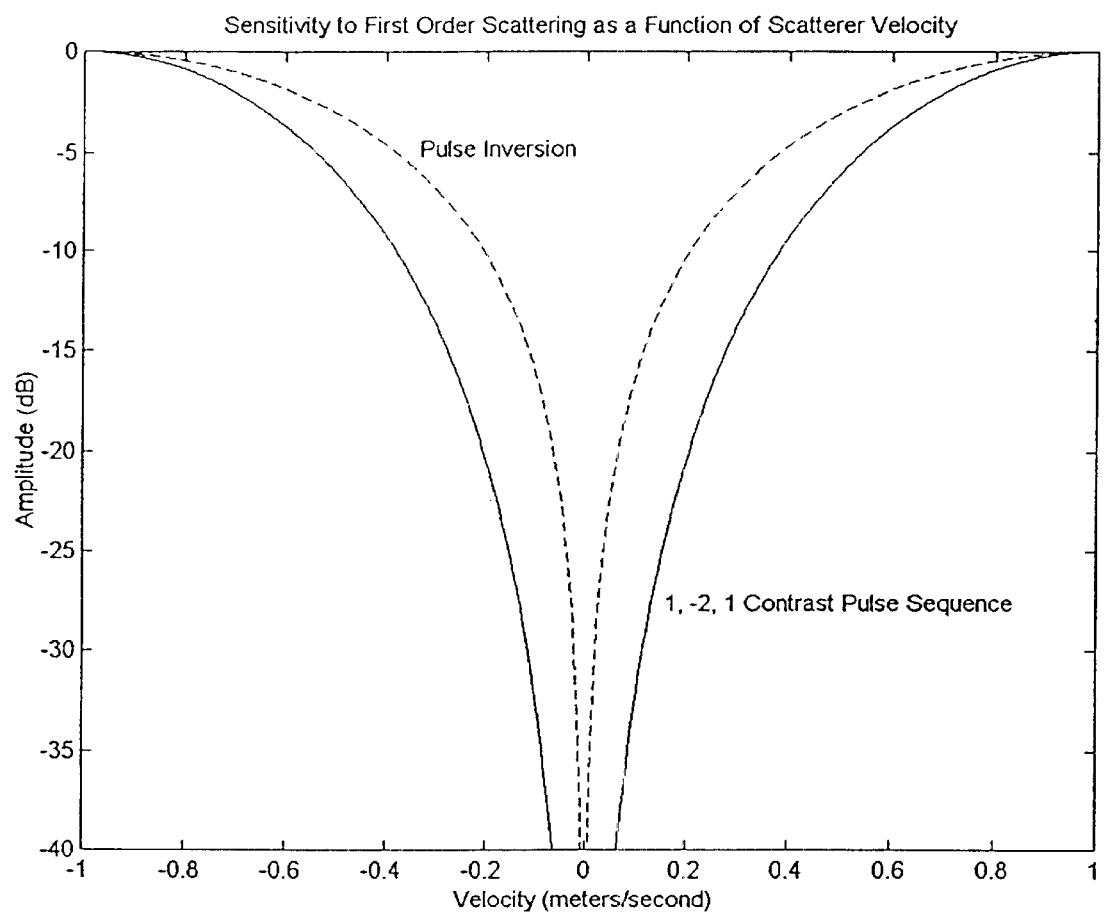
FIGS. 1–9 are graphs illustrating the sensitivity of selected contrast pulse sequences to echoes of selected orders from moving scatterers.

Current contrast agent detection schemes that rely on the nonlinear scattering from contrast agent detect only even order scattering (in the case of pulse inversion as imaging described in Hwang U.S. Pat. No. 5,951,478, and Chapman U.S. Pat. No. 5,632,277) or are designed to isolate a particular order of scattering (as described in the paper by Bruno Haider and Richard Chiao entitled "Higher Order Nonlinear Ultrasonic Imaging"). The CPS embodiments described below allow detection of both odd and even order scattering, while excluding scattering of an undesirable order. All of these techniques (pulse inversion, the Haider technique, and CPS) rely on firing several pulses in one direction and then combining the received signals coherently. If all targets in the insonified field are stationary, then this combining of signals can completely reject scattering of a particular order. (E.g., for stationary scatterers, pulse inversion completely rejects all odd order scattering.) However, if targets are moving, then this rejection is incomplete and can result in reduced specificity.

One embodiment of the invention is directed to a method of ultrasound imaging, in which a sequence of pulses is fired into the body, where at least two pulses of the sequence have different amplitudes and phase, but no two pulses of the sequence have the same amplitude and opposite phase. In a preferred embodiment, the sequence of pulses is fired along the same scan line, but the sequence of pulses can be fired in an alternating fashion as described below. The sequence of pulses includes at least two pulses. Most preferably, it includes at least three pulses, one of which is transmitted at twice the amplitude of the other two, and the pulse transmitted at twice the amplitude of the other two pulses is 180 degrees out of phase with the other two pulses. A most preferred pulse sequence can be represented as $\{1, -2, 1\}$, wherein the coefficients 1, 2, and 1 represent the relative amplitudes of the pulses, and the minus sign represents the 180 degree phase shift of the second pulse. Ideally, the phase shift is precisely 180 degrees, but variations from the ideal are acceptable as long as first order signals are at least 6 dB below the second order signals after the receive weighting and summing. Preferably, the first order signals are at least 20 dB below the second order signals, and most preferably they are below the noise floor. The noise floor is defined as the root-mean-square amplitude of electronic noise due to system electronics.

In another embodiment, the CPS includes at least six pulses, two of which are transmitted at twice the amplitude of the other four. Preferably, the pulses comprise a first and a second time-interleaved series of three pulses, wherein each pulse of the second time-interleaved series is 90 degrees out of phase with a corresponding one of the first time-interleaved series of pulses. One such pulse sequence can be represented as $\{1, i, -2, -2i, 1, i\}$. The coefficients 1, 2, and 1 represent the relative amplitude of the pulses, the minus sign represents the 180 degree phase shift of the second pulse in each series of pulses, and the i represents the 90 degrees phase shift between corresponding pulses of each of the interleaved series of pulses.

Yet another embodiment of the invention is directed to firing a sequence of pulses having different amplitude and phase from each other into a body, and weighting and summing the received echoes from the body such that only linear echoes from scatterers are significantly suppressed. The CPS $\{2, 1, -1, -2\}$ with receive weightings of $\{3, 8, 24, -5\}$ is an example of such a sequence. Echoes are significantly suppressed when suppressed by at least 6 dB relative to scattering of the order of interest, but preferably when suppressed by at least 20 dB, and most preferably when suppressed to or below the noise floor.

Another embodiment of the invention is directed to firing a sequence of at least three pulses into a body along a scan line, where at least two pulses of the sequence have the same amplitude and phase as each other, and at least two pulses of the sequence have different amplitudes from each other. Preferably, the at least two pulses that have different amplitudes from each other also have the same phase as each other. Preferably, the method further comprises receiving echoes from each of the pulses in the sequence, and weighting and summing the received echoes such that only linear echoes are significantly suppressed. A particularly preferred pulse sequence is $\{1, 2, 1\}$, wherein the coefficients 1, 2, and 1 represent the relative amplitude of the pulses, with receive weights of 1, −1, 1.

Yet another embodiment is directed to selecting (1) power levels for transmitting a sequence of ultrasound pulses into a body and (2) receive weights for applying to echoes received from scatterers in the body. The selections are made such that the selected transmitted power levels and receive weights preserve echo information from at least second and third order scattering and suppress echo information from first order scattering. The selections are used to transmit, receive and ultimately display an image. Preferably, two zeroes in the range of zero velocity ±30 cm/second result from the selection process. Most preferably, the selecting step results in placing at least two zeroes at zero velocity.

The following discussion considers transmitted pulses of the form $p_k(t)=a_k a(t)\cos(\omega_0 t)$, where $a_k$ defines the amplitude and phase of the pulse, $\alpha(t)$ defines the envelope of the transmitted signal, and $\cos(\omega_0 t)$ represents the carrier frequency. We assume that the response (ignoring propagation delays) of a contrast agent is given by:

$$s_k(t)=\alpha_1 p_k(t)+\alpha_2 p_k^2(t)+\alpha_3 p_k^3(t)+\alpha_4 p_k^4(t)+$$

For pulse inversion techniques, where $a_1=1$ and $a_2=-1$, $$s_1(t)+s_2(t)=2\alpha_2 a^2(t)\cos^2(\omega_0 t)+2\alpha_4 a^4(t)\cos^4(\omega_0 t)+$$

The resulting signal has no odd order scattering. However, for a CPS sequence such as $\{1, -2, 1\}$, where $a_1=a_3=0.5$, $a_2=-1$, and the minus sign indicates a phase shaft of 180° relative to the first pulse of the sequence, the resulting signal is given by:

$$s_1(t)+s_2(t)+s_3(t)=-0.5\alpha_2 a^2(t)\cos^2(\omega_0 t)-0.75\alpha_3 a^3(t)\cos^3(\omega_0 t)-0.875\alpha_4 a^4(t)\cos^4(\omega_0 t)+$$

which contains both even and odd order scattering.

Although the third harmonic signal may seem to be of primarily academic interest, much of the third harmonic signal appears at the fundamental frequency. (Note the trigonometric identity $\cos^3(\omega_0 t)=0.75\cos((\omega_0 t)+0.25\cos(3\omega_0 t))$.) Therefore much of the third harmonic scattering appears at the fundamental frequency and can easily be detected.

Note that the third order scattering components (that appear at the fundamental frequency) cannot be detected by pulse sequences consisting of equal amplitude pulses with opposite (0 degree and 180 degree) phase. Only by varying the amplitude between at least two of the transmitted signals can one detect third order nonlinearities at the fundamental frequency while suppressing first-order scattering. (One can detect third order scattering at 3 times the fundamental frequency while suppressing the first-order scattering by transmitting pulses of constant amplitude if the phase between at least two of the transmitted pulses differs by an amount other than 0 degree or 180 degree.)

Using a six pulse CPS, it is possible to suppress both the fundamental and second harmonic signals and image only third order and higher scattering, opening up the possibility of improving the specificity of contrast agent detection with nonlinear scattering. For this six pulse CPS, the pulses can be described by:

$$p_1(t)=0.5a(t)\cos(\omega_0 t)$$

$$p_2(t)=0.5a(t)\sin(\omega_0 t)$$

$$p_3(t)=-a(t)\cos(\omega_0 t)$$

$$p_4(t)=-a(t)\sin(\omega_0 t)$$

$$p_5(t)=0.5a(t)\cos(\omega_0 t)$$

$$p_6(t)=0.5a(t)\sin(\omega_0 t)$$

This pulse sequence can be written as, $\{1, i, -2, -2i, 1, i\}$, where the minus sign represents a phase shift of 180° and i represents a phase shift of 90° relative to the first pulse of the sequence. After summing up the received signals (with uniform receive weighting) the result would be:

$$s_1(t)+s_2(t)+s_3(t)+s_4(t)+s_5(t)+s_6(t)=-0.75\alpha_3 a^3(t)\cos^3(\omega_0 t)-0.75\alpha_3 a^3(t)\sin^3(\omega_0 t)+2.25\alpha_4 a^4(t)\cos^4(\omega_0 t)+$$

which contains only scattering from third order and higher terms. There are shorter pulse sequences such as $\{1, i, -2, -2i\}$ with receive weights $\{2, 2, 1, 1\}$ that can reject both the first and second order scattering. The six pulse sequence was chosen because it is simple and also provides good immunity to motion artifacts generated from insufficient suppression of signals of undesired orders (such as first) from moving scatterers.

In addition to the advantage of rejecting specific orders of scattering, contrast pulse sequences can be designed to reduce artifacts due to motion. The CPS $\{1, -2, 1\}$ discussed above is more effective at rejecting first order scattering from moving targets than pulse inversion. In FIG. 1 we plot the sensitivity to first order scattering as a function of scatterer velocity for both pulse inversion and a $\{1, -2, 1\}$ contrast pulse sequence. (For all graphs of sensitivity versus scatterer velocity, the assumed ultrasound pulse center frequency is 3.85 MHz, the assumed pulse repetition interval is 200 microseconds, and the assumed velocity of sound is 1.54 mm/microsecond.) Note that for slowly moving scatterers, the rejection of first order scattering by the CPS technique is 20 dB better than pulse inversion. If one thinks of the transmitted amplitudes as coefficients of a filter, then the improved rejection of first order scattering from moving scatterers is easily understood because the $\{1, -2, 1\}$ sequence has 2 zeros at zero velocity, while the pulse inversion sequence $\{1, -1\}$ places only one zero at zero velocity.

Figure 2:
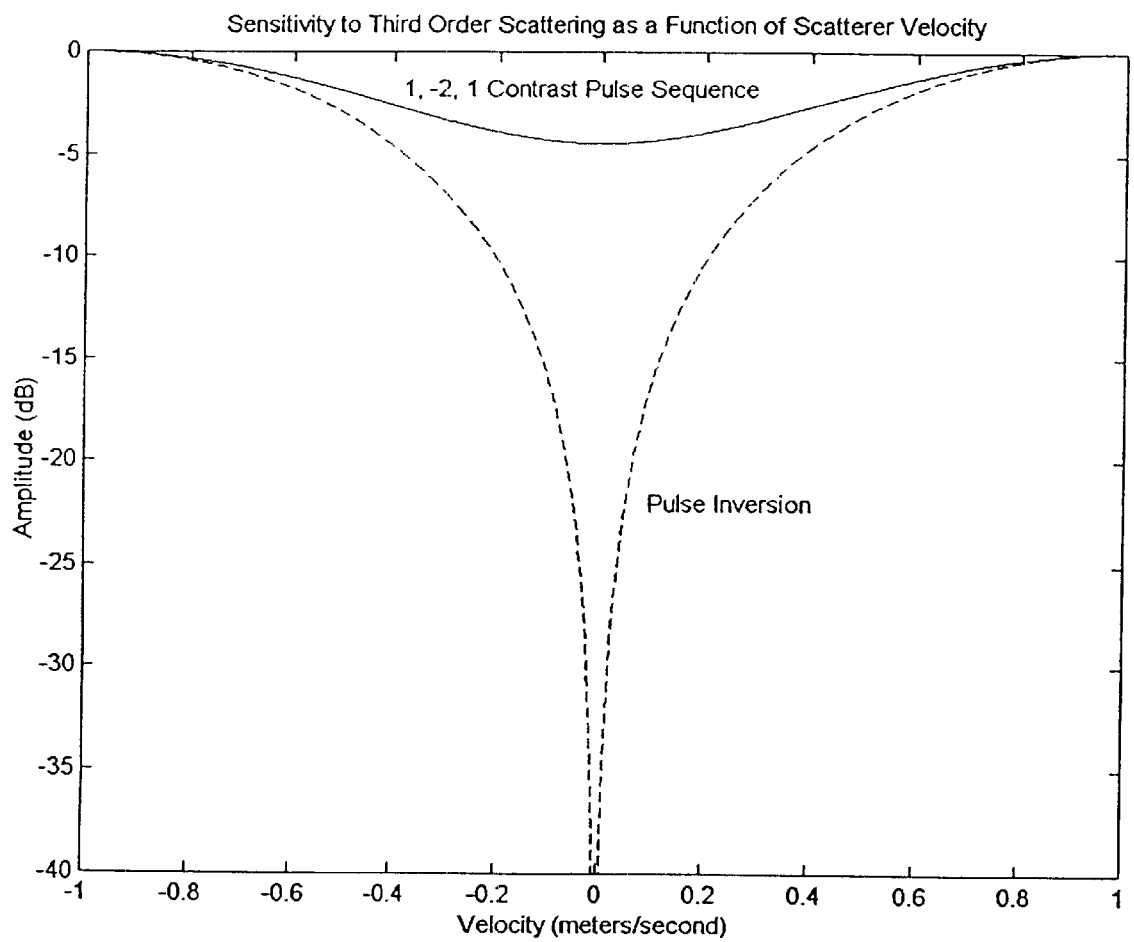
Figure 3:
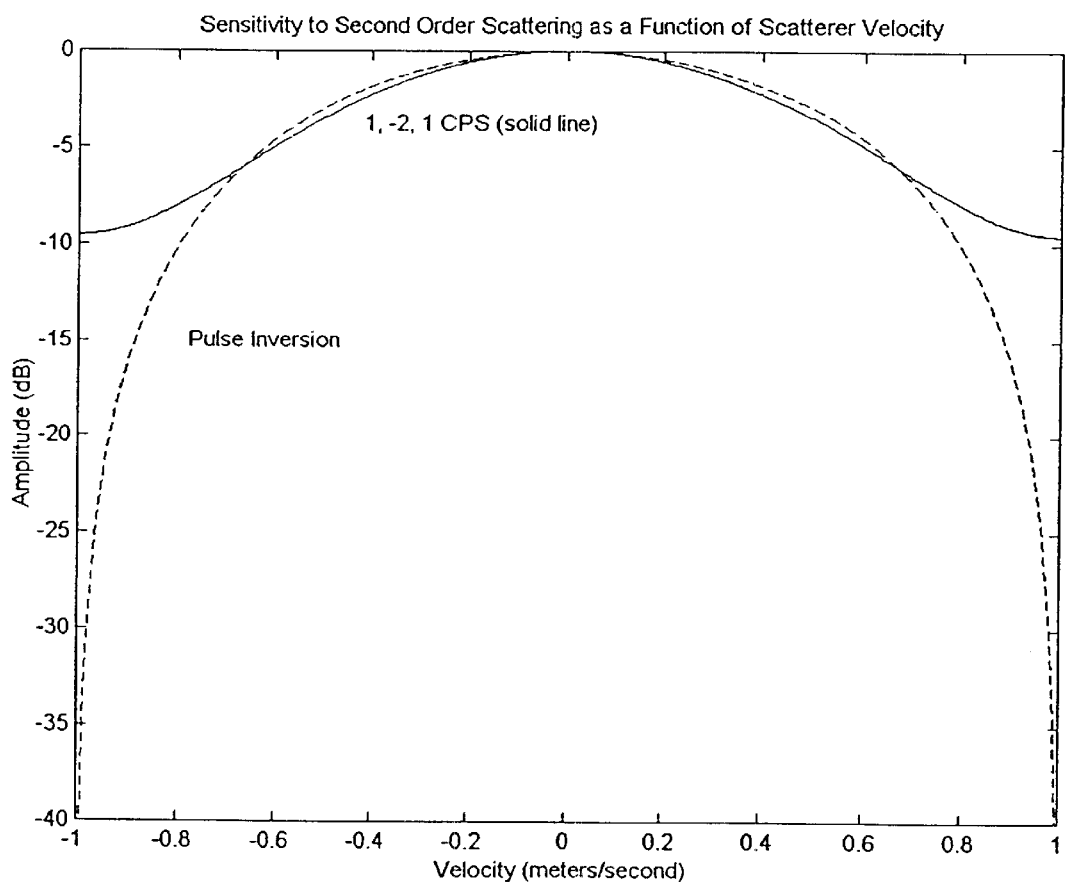

For third order scattering (shown in FIG. 2), the CPS $\{1, -2, 1\}$ has excellent sensitivity while pulse inversion has poor sensitivity to third order scattering. As shown in FIG. 3, both the CPS $\{1, -2, 1\}$ and the pulse inversion sequence have good sensitivity to second order scattering.

An alternative to imaging contrast agents via higher order nonlinear response is the loss of correlation (LOC) effect. The LOC effect relies on the first pulse altering the contrast agent in some way that is detected by the second pulse. The contrast pulse sequence $\{1, -2, 1\}$ has very good sensitivity to the LOC effect because the first pulse alters the contrast agent (usually by destroying, releasing encapsulated gas, modifying the characteristics of the agent shell, or moving the agent), so the response to the second pulse (for first order scattering) is not twice the amplitude and of the opposite phase as the response to the first pulse. Similarly, the response to the third pulse is not equal to the response to the first pulse, again because of the modification of the contrast agent. Therefore, when the responses are summed, the result is not zero. For tissue, which does not change between the insonifications, the resulting LOC signal is zero (neglecting motion). In the presence of tissue motion, the CPS $\{1, -2, 1\}$ has the same improved rejection of first order scattering over the pulse inversion sequence $\{1, -1\}$ as shown in FIG. 1.

As the name implies, contrast pulse sequences are sequences of pulses that can be used for conventional B-mode imaging. Such pulses include:

unipolar binary pulses, bipolar binary pulses, pulses achieved by modulating a carrier frequency, as described in Hossack U.S. Pat. No. 5,608,690, binary pulses that are smoothed by the non-linear response of elements in the transmit path, and pulses generated by storing a waveform in memory and then presenting the contents of the memory (in sequence) to a digital-to-analog converter.

Although we prefer to use pulses with characteristics (center frequency, bandwidth, and shape) that are similar to those used for conventional B-mode imaging, no particular pulse shape is required for contrast pulse sequences. For this reason, any pulse shape or pulse generation technique can be used with this invention.

When characterizing a contrast pulse sequence we frequently use a notation such as {1, −2, 1}. This notation describes both the amplitude and phase of the transmitted pulses. We recognize that the actual transmitted amplitudes are normalized to the maximum allowable output, as determined by either system limitations (peak voltages available, maximum pulser power, etc.), regulatory limits on acoustic output (MI, ISPTA, TI, etc.), or the desire by the clinician to limit acoustic output to achieve a desired result during the ultrasound exam (limiting exposure of the patient, avoiding destruction of contrast agents, etc.). The notation also depicts the phase of the transmitted pulses, using a negative sign to indicate a 180 degree phase shift and the symbol i to indicate a 90 degree phase shift. (Phases are not limited to 0, 90, 180, and 270 degrees. Any arbitrary phase can be used for transmit or receive.) In Table 1 we present various characteristics of several contrast pulse sequences.

and has a phase of 90 degrees in this embodiment.) Note, the use of the start of transmission as the time reference for determining phase is convenient, but arbitrary. Any time reference that is the same for all transmitted pulses can be used. For unipolar binary waveforms, this phasing of the CPS pulses is achieved by delaying the pulses as appropriate. A 90 degree phase corresponds to a delay of ¼ of the period of the center frequency of the pulse, and a 180 degree phase corresponds to a delay of one-half cycle at the center frequency of the pulse. For bipolar binary waveforms, a phase of 90 degrees is again achieved by delaying the pulse by ¼ of the period of the center frequency of the pulse, and a 180 degree phase can be achieved by inverting the pulse.

Upon reception of echoes resulting from each transmitted pulse, the received echoes are multiplied by receive weighting factors (which may vary in amplitude and phase for each transmitted pulse), and these weighted received signals are summed to produce the composite output signal. These receive weighting factors are chosen to suppress specific orders of scattering. For example, if only first order scatter-

TABLE 1

Exemplary Contrast Pulse Sequences

| CPS name | Transmitted Amplitude (fraction of maximum output) | Transmitted Phase | Receive Weighting Amplitude | Receive Weighting Phase | Sensitivity to $1^{st}$ order signal | Sensitivity to $2^{nd}$ order signal | Sensitivity to $3^{rd}$ order signal |
|---|---|---|---|---|---|---|---|
| {1, −2, 1} | ½, 1, ½ | 0, 180, 0 | 1, 1, 1 | 0, 0, 0 | 0 | 1.5 | ¾ |
| {1, i, −2, −2i, 1, i} | ½, ½, 1, 1, ½, ½ | 0, 90, 180, 270, 0, 90 | 1, 1, 1, 1, 1, 1 | 0, 0, 0, 0, 0, 0 | 0 | 0 | $\frac{3\sqrt{2}}{4}$ |
| {2, 1, −1, −2} | 1, ½, ½, 1 | 0, 0, 180, 180 | 3, 8, 24, 5 | 0, 0, 0, 180 | 0 | 6 | 6 |
| {1, i, −2, −2i} | ½, ½, 1, 1 | 0, 90, 180, 270 | 2, 2, 1, 1 | 0, 0, 0, 0 | 0 | 0 | $\frac{3\sqrt{2}}{4}$ |
| {1, −2, 1, −2, 1} | ½, 1, ½, 1, ½ | 0, 180, 0, 180, 0 | 1, 2, 6, 2, 1 | 0, 0, 0, 0, 0 | 0 | 6 | 3 |
| {1, −2, 2, −2, 1} | ½, 1, 1, 1, ½ | 0, 180, 0, 180, 0 | 1, 2, 6, 2, 1 | 0, 0, 0, 0, 0 | 0 | 7.5 | ¾ |
| {1, −2} | ½, 1 | 0, 180 | 2, 1 | 0, 0 | 0 | 1.5 | ¾ |
| {1, 2, 1} | ½, 1, ½ | 0, 0, 0 | 1, 1, 1 | 0, 180, 0 | 0 | 2 | 6 |
| {3, −5, 4, −5} | 0.6, 1, 0.8, 1 | 0, 180, 0, 180 | 5/3, 3, 3.75, 1 | 0, 0, 0, 0 | 0 | 7 | 1.72 |
| {2, −5, 3, −5} | 0.4, 1, 0.6, 1 | 0, 180, 0, 180 | 2.5, 3, 5, 1 | 0, 0, 0, 0 | 0 | 6.2 | 2.76 |

The conventional name (a sequence of numbers) for each contrast pulse sequence is listed in the first column. The number of pulses in each contrast pulse sequence is determined by the number of numerical entries in the name. For example, the first CPS {1, −2, 1} has three pulses, while the second CPS {1, i, −2, −2i, 1, i} has 6 pulses (note that 'i', the square root of negative 1, is considered a number in this notation). The transmitted amplitude (relative to the peak desired output) for each of the pulses is listed in the second column. The third column provides the corresponding phase for each of the transmitted pulses. For pulses generated by modulating a carrier frequency, this phase is the phase of the carrier relative to the time at which transmission of the pulse begins. (For example, a carrier that is at its positive peak when transmission begins is a cosine wave and has zero phase in this embodiment, while a carrier that is at zero and has a positive slope when transmission begins is a sine wave ing is to be suppressed, then the sum of each transmit amplitude times the respective receive amplitude should equal zero.

A good method for representing the complex nature of both the transmit amplitude and the receive weights is to use complex notation, in which a pulse with a transmit amplitude of ½ and a transmit phase of 180 degrees is represented by −½. Similarly, a pulse with a transmit amplitude of 2 and a transmit phase of 90 degrees is represented by 2i. This notation easily extends to other phase angles by combining real and imaginary values, for instance, a pulse with an amplitude of 2 and a phase of 45 degrees would be represented by ($\sqrt{2}+i\sqrt{2}$).

Looking at the first contrast pulse sequence of Table 1, the complex transmit amplitudes are ½, −1, and ½. The complex receive weights are all 1. Therefore, the sum of the complex transmit amplitudes times the complex receive weights is:

$$(\tfrac{1}{2} \times 1) + ((-1) \times 1) + (\tfrac{1}{2} \times 1) = \tfrac{1}{2} + (-1) + \tfrac{1}{2} = 0.$$

Therefore, first order scattering will be suppressed in the composite output signal by this complex pulse sequence. The sensitivity to first order scattering for each contrast pulse sequence is listed in Table 1.

To determine the sensitivity of a contrast pulse sequence to second order scattering, the complex transmit pulse amplitudes are first squared, then multiplied by the corresponding complex receive weights and summed. Using the $\{1, -2, 1\}$ sequence again, we find that the second order sensitivity is given by:

$$((\tfrac{1}{2})^2 \times 1) + ((-1)^2 \times 1) + ((\tfrac{1}{2})^2 \times 1) = \tfrac{1}{4} + 1 + \tfrac{1}{4} = \tfrac{3}{2}.$$

Similarly, the third order sensitivity is determined by squaring the complex transmit amplitudes then multiplying by the complex conjugate of the complex transmit amplitude before weighting with the complex receive amplitudes and summing. The $\{1, -2, 1\}$ CPS third order sensitivity is thus:

$$((\tfrac{1}{2})^3 \times 1) + ((-1)^3 \times 1) + ((\tfrac{1}{2})^3 \times 1) = \tfrac{1}{8} + (-1) + \tfrac{1}{8} = -\tfrac{3}{4}.$$

Since we are not interested in the phase of the sensitivity, the corresponding entry in the table does not include the negative sign in the result.

Turning to the second contrast pulse sequence $\{1, i, -2, -2i, 1, i\}$ of Table 1, we see that the sensitivity to both first and second order scattering is zero:

$$(\tfrac{1}{2} \times 1) + (1i/2 \times 1) + ((-1) \times 1) + ((-1i) \times 1) + (\tfrac{1}{2} \times 1) + (1i/2 \times 1) = \tfrac{1}{2} + (-1) + \tfrac{1}{2} + 1i/2 + (-1i)1i/2 = 0;$$

$$((\tfrac{1}{2})^2 \times 1) + ((1i/2)^2 \times 1) + ((-1)^2 \times 1) + ((-1i)^2 \times 1) + ((\tfrac{1}{2})^2 \times 1) + ((1i/2)^2 \times 1) = \tfrac{1}{4} + -\tfrac{1}{4} + 1 + (-1) + \tfrac{1}{4} + -\tfrac{1}{4} = 0.$$

The third order sensitivity for this sequence is given by:

$$((\tfrac{1}{2})^3 \times 1) + ((1i/2)^3 \times 1) + ((-1)^3 \times 1) + ((-1i)^3 \times 1) + ((\tfrac{1}{2})^3 \times 1) + ((1i/2)^3 \times 1) =$$

$$\tfrac{1}{8} + -1i/8 + (-1) + (1i) + \tfrac{1}{8} + -1i/8 = -\tfrac{3}{4} + 3i/4.$$

In the table we have once again shown the magnitude of the sensitivity because we are not interested in the phase.

Evaluating the contrast pulse sequence $\{2, 1, -1, -2\}$ with non-unity receive weighting, we obtain the following sensitivities for first through third order scattering:

$$(1 \times 3) + (\tfrac{1}{2} \times 8) + (-\tfrac{1}{2} \times 24) + ((-1) \times (-5)) = 3 + 4 + (-12) + 5 = 0; \quad (1^{st} \text{ order})$$

$$(1^2 \times 3) + ((\tfrac{1}{2})^2 \times 8) + ((-\tfrac{1}{2})^2 \times 24) + ((-1)^2 \times (-5)) = 3 + 2 + 6 + (-5) = 6; \quad (2^{nd} \text{ order})$$

$$(1^3 \times 3) + ((\tfrac{1}{2})^3 \times 8) + ((-\tfrac{1}{2})^3 \times 24) + ((-1)^3 \times (-5)) = 3 + 1 + (-3) + 5 = 6. \quad (3^{rd} \text{ order})$$

Figure 4:
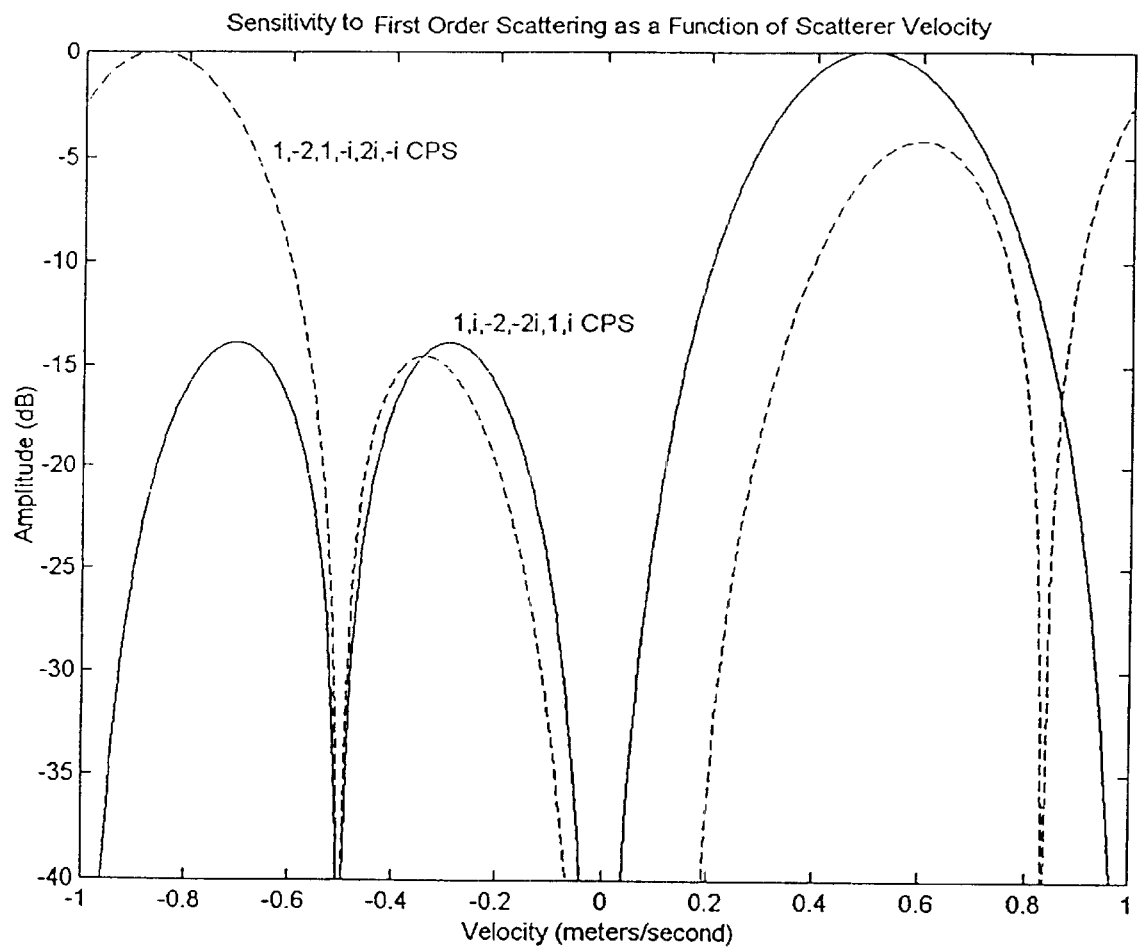
Figure 5:
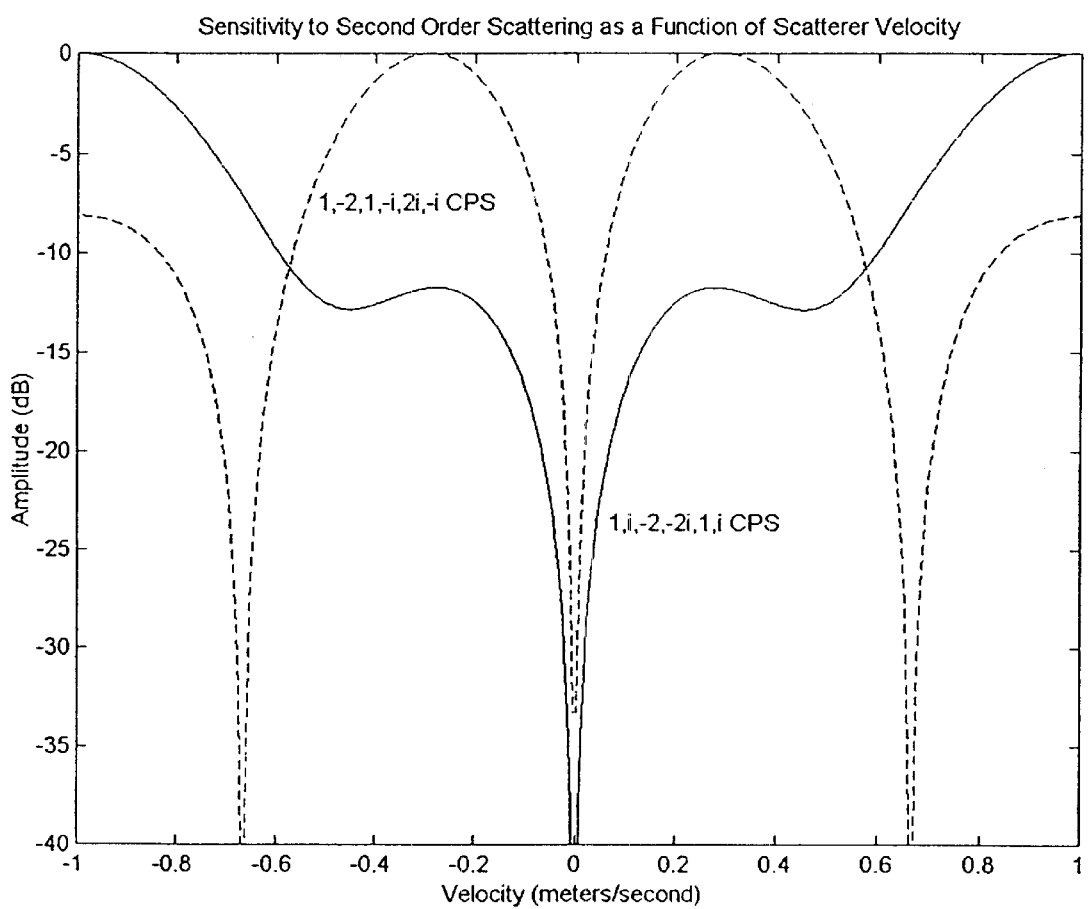
Figure 6:
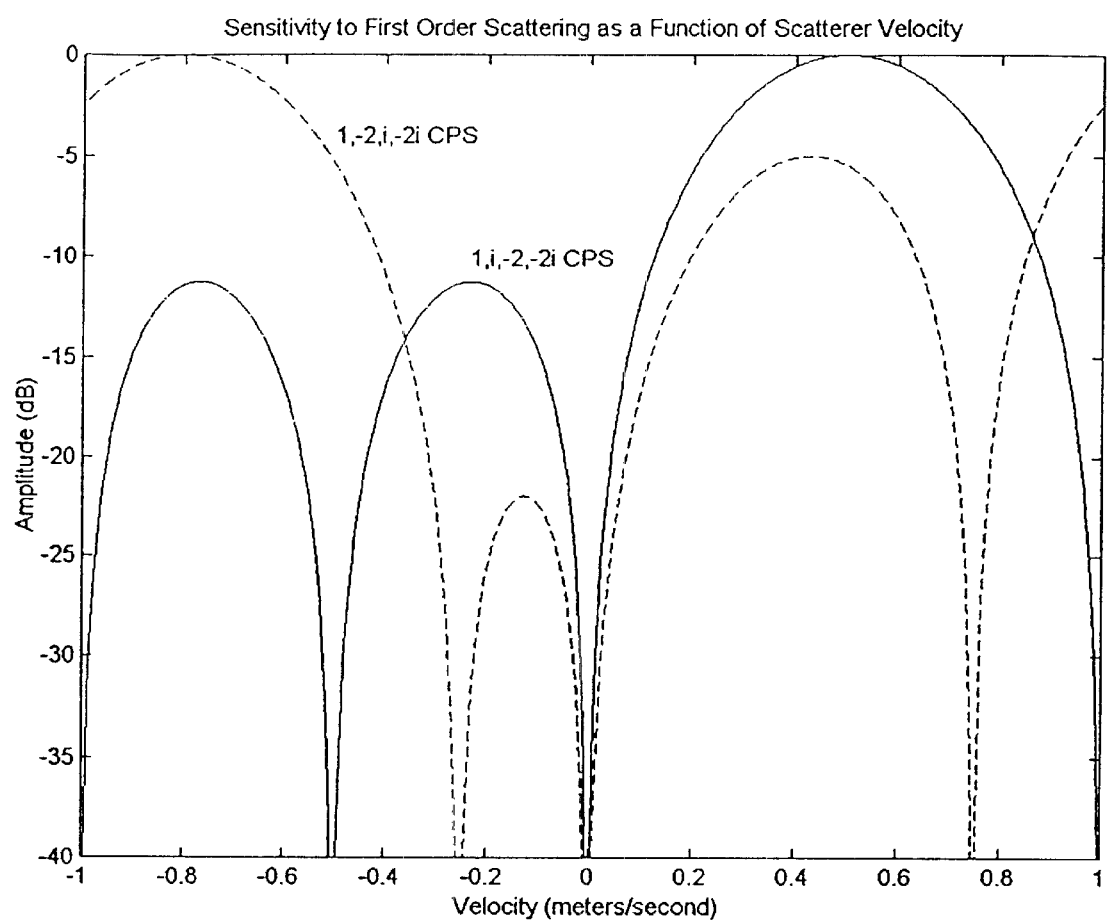
Figure 7:
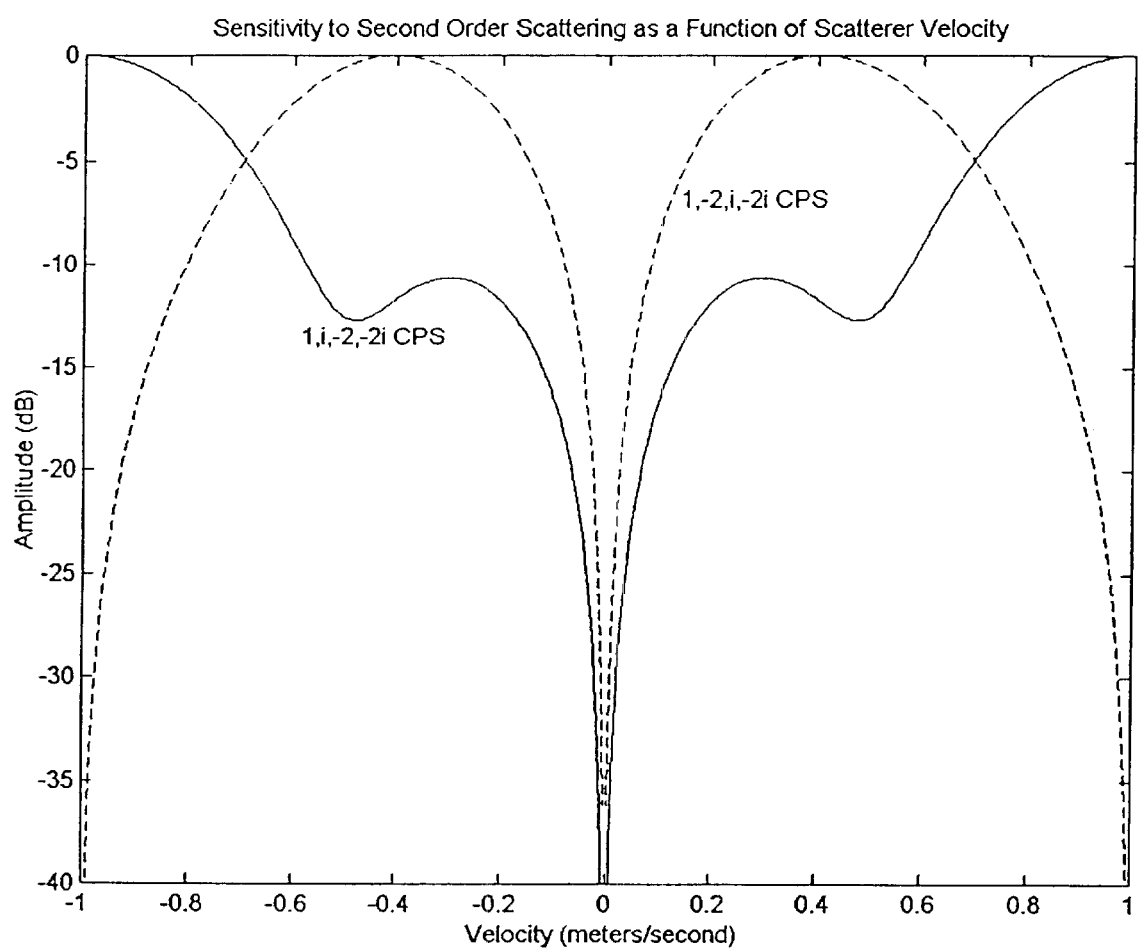

As the preceding analysis shows, the particular order in which the pulses are transmitted does not affect the rejection of specific orders of scattering for stationary scatterers. However, this order is important if motion is present. As shown previously, contrast pulse sequences can reject specific orders of scattering from moving scatterers better than previous techniques such as the pulse inversion technique. In addition, changing the order of pulses in the sequence will affect rejection of signals from moving scatterers. In FIG. 4 we show a comparison of the sensitivity to first order scattering for two different pulse sequences $\{1, i, -2, -2i, 1, i\}$ and $\{1, -2, 1, -i, 2i, -i\}$. Note that for slow moving (less than 30 cm/second) scatterers, the $\{1, -2, 1, -i, 2i, -i\}$ CPS always has less sensitivity (better rejection) than the $\{1, i, -2, -2i, 1, i\}$ CPS. Looking at FIG. 5, however, we see that the $\{1, i, -2, -2i, 1, i\}$ CPS has better rejection of second order scattering (for slow moving scatterers) than the $\{1, -2, 1, -i, 2i, -i\}$ CPS. Similar results from rearranging the $\{1, i, -2, -2i\}$ CPS can be seen in FIGS. 6 and 7. When suppression of more than one order of scattering is desired, the order of scattering that is least desirable is determined, and then the CPS that best suppresses this order of scattering can be chosen.

Figure 8:
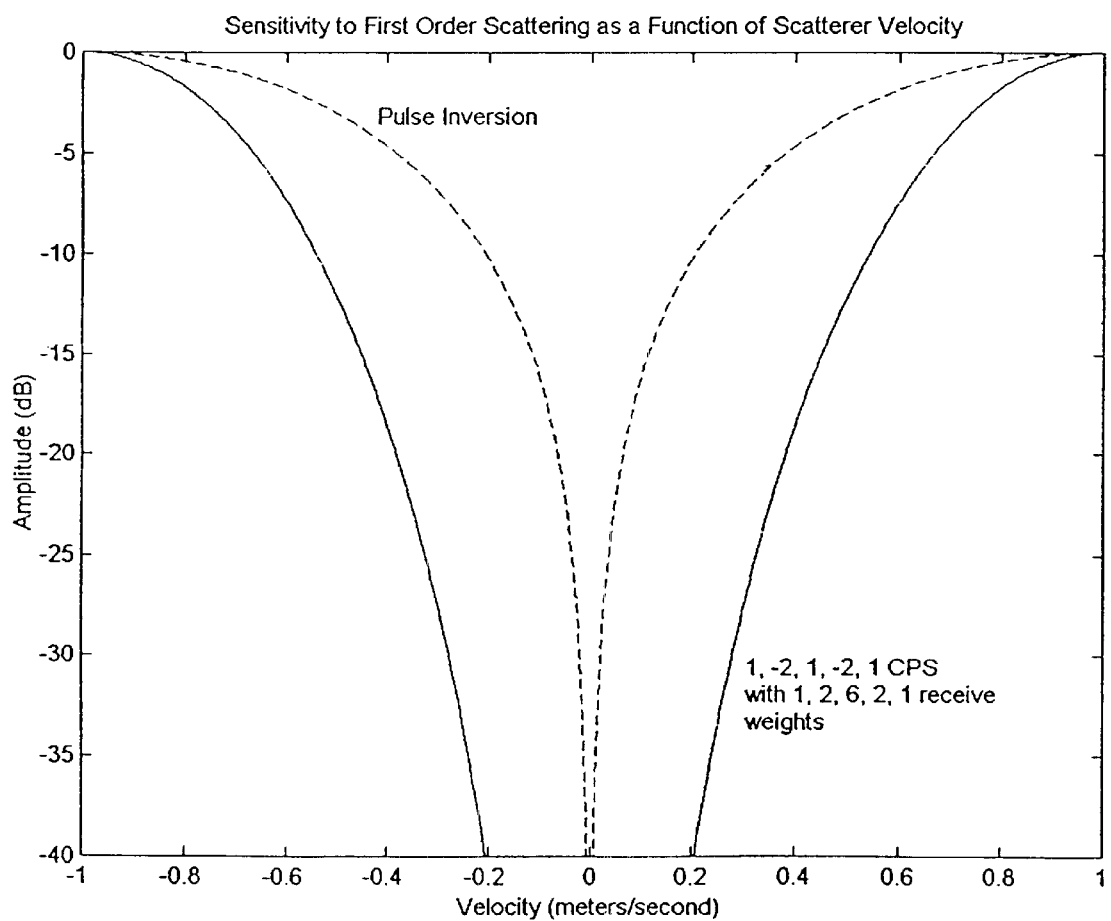

Finally, a simple contrast pulse sequence $\{1, -2, 1\}$ can be extended to $\{1, -2, 1, -2, 1, \ldots\}$ to improve rejection of signals from moving scatterers. In FIG. 8 we show the case of the sequence $\{1, -2, 1, -2, 1\}$ with receive weights $\{1, 2, 6, 2, 1\}$ as compared with a conventional pulse inversion sequence. The improved motion rejection is gained by using more pulses (as improved rejection of clutter signals is improved with more pulses in flow imaging), but unlike the straight-forward extension of pulse inversion (the sequence $\{1, -1, 1, -1, 1\}$) the contrast pulse sequence retains sensitivity to third order scattering.

When designing a contrast pulse sequence to achieve optimal rejection of first order scattering from slowly moving scatterers, the product of the complex transmit amplitudes with the complex receive weights can be thought of as a filter. For a two pulse sequence, with transmit amplitudes of $\{1, -1\}$ and receive weights of $\{1, 1\}$, this product is $\{1, -1\}$. As is well known in signal processing, a $\{1, -1\}$ filter has zero response at DC (which corresponds to zero velocity). In signal processing nomenclature, one can develop a (longer) filter with multiple zeros at DC by repetitive convolutions of the simple $\{1, -1\}$ filter. For example, convolving $\{1, -1\}$ with $\{1, -1\}$ yields $\{1, -2, 1\}$, which has 2 zeros at DC, and therefore better rejection of first order scattering from slowly moving scatterers. (See FIG. 1.) Additional zeros can be added by further convolutions, for example:

$\{1-2\ 1\}\circledx\{1-1\}=\{1-3\ 3-1\}$, which has 3 zeros at DC;

$\{1-3\ 3-1\}\circledx\{1-1\}=\{1-4\ 6-4\ 1\}$, which has 4 zeros at DC; and $\{1-4\ 6-4\ 1\}\circledx\{1-1\}=\{1-5\ 10-10\ 5-1\}$, which has 5

It is possible to simply use the values listed in the above examples as the complex transmit amplitudes for a contrast pulse sequence. However, such an approach has two disadvantages: there is no sensitivity to odd order harmonics for even pulse sequences; and the signal-to-noise ratio for all longer sequences is unnecessarily low due to the wide range of transmit amplitudes required. Therefore, we prefer to keep the transmit amplitudes between 1 and 2 inclusive, and to use the receive weights to complete the filter for motion rejection. Therefore, one effective five element CPS designed for motion suppression is $\{1, -2, 1, -2, 1\}$ with receive weights of $\{1, 2, 6, 2, 1\}$. The performance of this CPS at rejecting motion is shown in FIG. 8. Note that another five element CPS with equal motion suppression is $\{1, -2, 2, -2, 1\}$ with receive weights of $\{1, 2, 3, 2, 1\}$; however, this CPS has much less sensitivity to third order scattering (see Table 1).

Transmit and receive weights can also be adjusted to preferentially improve the SNR of one order compared to another desired order while maintaining adequate suppression of undesired orders. Two examples of sequences are the last two sequences in Table 1. These two sequences have identical suppression of fundamental signals but the ratio of second harmonic energy to cubic fundamental energy differs.

In addition to placing zeros at DC (zero velocity) to eliminate scattering from slowly moving scatterers, one can also insert zeros near zero velocity. This allows widening of the range of velocities that the CPS rejects. Accordingly, in most preferred embodiments of the invention, at least two zeroes are placed in the band or range of zero velocity ±30 cm/second.

Figure 9:
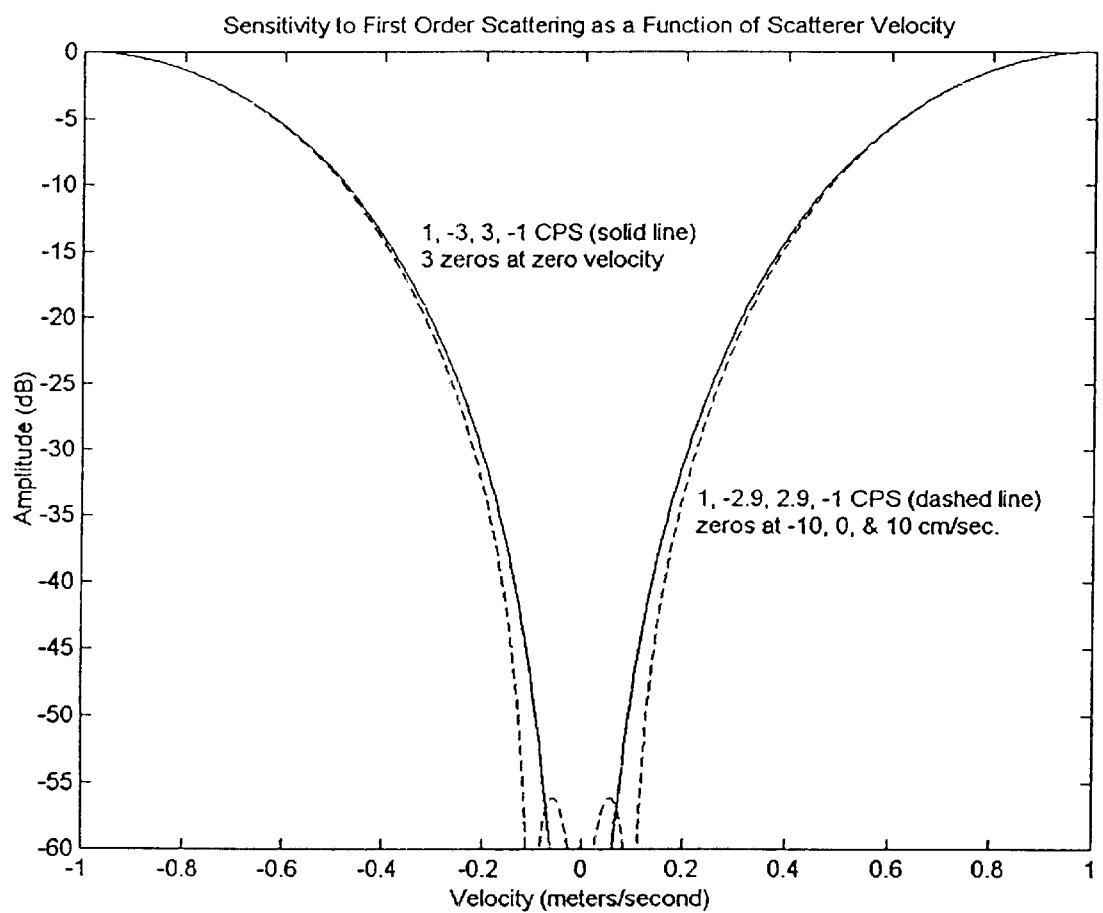

For example, the sequence {1, −2.9, 2.9, −1} has one zero at zero velocity and two others at velocities of ±10 cm/second, given the assumptions about pulse center frequency (3.85 MHz), pulse repetition interval (200 microseconds), and the velocity of sound (1.54 mm/microsecond). In FIG. 9 we show the sensitivity of the {1, −2.9, 2.9, −1} CPS and compare it with the sequence {1, −3, 3, −1} that has three zeroes at zero velocity.

The previous discussion has assumed that sequential transmissions of pulses in a contrast pulse sequence are steered in the same, or substantially the same, direction. This approach ensures that the same scatterers are insonified with each pulse and therefore that signals arising from sequential pulses differ only as a result of changes in the transmitted pulse. (Note that small changes in insonification direction can be made with this approach, such that changes in the received signals due to the change in insonification direction are similar in amplitude to the changes in the received signals due to noise, without degrading the performance of contrast pulse sequences.) U.S. patent application Ser. No. 09/282,396, assigned to the assignee of the present invention, describes the Alternating Line Phase technique, whereby signals arising from transmission along two different lines can be processed to eliminate scatterering of an undesirable order. In accordance with an embodiment of this invention, an application of Alternating Line Phase to CPS is to split one of the complex contrast pulse sequences into two sequences, and to transmit these two different sequences along two adjacent scan line directions. As an example, the {1, i, −2, −2i, 1, i} CPS can be split into two sequences {1, −2, 1} and {i, −2i, i}. The real sequence and the imaginary sequence are transmitted along adjacent scan lines, and the received signals from the adjacent lines (after receive weighting and summing) are summed. The individual lines reject first order scattering, and when the signals from adjacent transmit lines are added the second order scattering is rejected, just as with the original six pulse sequence. This technique can be extended to more lines and any number of pulses.

In accordance with another embodiment of the invention, it is possible to improve the signal to noise ratio (SNR) of CPS imaging while retaining image quality parameters (spatial resolution, clutter suppression, etc.) by using coding schemes to increase transmitted acoustic power without increasing peak transmitted acoustic amplitude.

Since CPS imaging transmits pulses of varying amplitudes, and the maximum amplitude is limited, pulses with lower amplitudes will result in signals with poorer SNR than those with the maximum amplitude. This can be corrected by using coding to lengthen the lower-amplitude pulses (without reducing axial resolution) until the amplitude (post pulse compression) of these pulses equals those of the maximum-amplitude pulses. A good candidate for this encoding is a chirp code, since chirp codes require only one pulse, and the shape of a chirped pulse can be easily predicted after nonlinear propagation or scattering. See the discussion in U.S. patent application Ser. No. 09/282,396, assigned to the assignee of the present invention. Using the example of a {1, −2} CPS, if the smaller amplitude pulse were lengthened to the point that its amplitude (post pulse compression) was the same as the larger pulse (in this case the complex receive weights would be {1, 1}), then the SNR (for all order scattering) would be increased by 4 dB. In general, it is preferred to use a longer code with lower peak amplitude pulses than with higher peak amplitude pulses.

Figure 10:
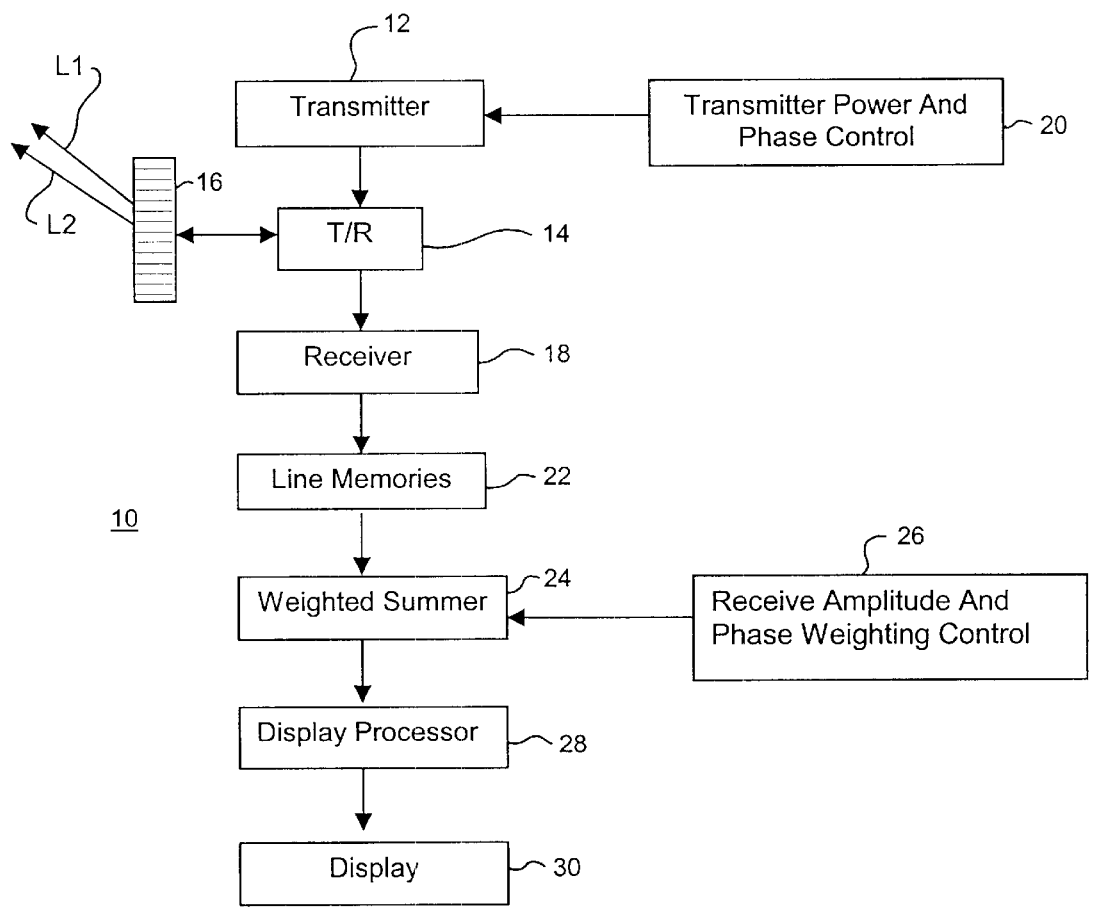
FIG. 10 is a block diagram of an ultrasonic imaging system suitable for use in contrast pulse imaging.

FIG. 10 shows a block diagram of a medical diagnostic ultrasonic imaging system that can be used to implement contrast pulse imaging as described above. The system 10 of FIG. 10 includes an ultrasonic transmitter 12 that is coupled to a transducer array 16 by a transmit/receive switch 14. The transmitter 12 applies transmit signals of selected waveform timing and phasing to the individual elements of the transducer array 16. In response, the transducer array 16 creates ultrasonic pressure waves, which conventionally are focused along one or more scan lines L1, L2. In the conventional manner, scan lines L1, L2 are steered across the region of interest by properly adjusting the phase and time delays of the transmit waveforms. Scatterers in the region of interest return ultrasonic energy to the transducer array 16, which in response forms echo signals that are applied by the transmit/receive switch 14 to a receiver 18. The receiver 18 applies appropriate phase and/or time delays to individual receive signals to cause the receive signals to add coherently from desired locations Within the region of interest.

The transmitter 12, transducer array 16 and receiver 18 can take any desired forms. The widest variety of techniques can be used to implement the transmitter 12, including both analog and digital techniques. The following U.S. patents, all assigned to the assignee of the present invention, provide examples of the types and approaches that can be used to implement the transmitter 12: U.S. Pat. Nos. 4,550,607, 4,699,009, 5,148,810, 5,608,690, and 5,675,554. If desired, the transmitter 12 may be used to form unfocused or only slightly focused pressure waves in the region of interest. These examples are of course not intended to be limiting in any way.

Similarly, the transducer array 16 can take any desired form. The transducer array 16 can be a 1-, 1.25-, 1.5-, 1.75- or 2-dimensional array. By way of example, the transducers described in any of the following U.S. patents (all assigned to the assignee of the present invention) can readily be adapted for use with this invention: U.S. Pat. Nos. 5,261, 408, 5,297,533, 5,410,208, 5,415,175, 5,438,998, 5,562,096, 5,657,295, 5,671,746, 5,706,820, 5,757,727, 5,792,058, 5,916,169, and 5,920,523. Once again, this list is not intended to be limiting, and any suitable transducer array can be used.

The receiver 14 can include beamformers implemented using any suitable technology. For example, the beamformers described in the following U.S. patents (all assigned to the assignee of the present invention) can readily be adapted for use with this invention: U.S. Pat. Nos. 4,550,607, 4,699, 009, and 5,555,534. Alternately, the receiver 14 can include one or more beamformers that form beams on a point-by-point basis rather than a scan-line basis. As before, these examples are not intended to be limiting.

As described above, the amplitude and phase of transmitted signals are controlled to provide the desired contrast pulse sequence. In the system 10 the transmitter power and phase control 20 applies control signals to the transmitter 12 to create transmit pulses of the desired power and phase. Transmitter power can be varied in any suitable manner, as for example by adjusting the voltage applied to individual transducer elements, or by adjusting the number of transducer elements (or transmit aperture) used to form a particular pulse.

Beamformed signals from the receiver 18 are stored in line memories 22. The line memories 22 can be formed as physically separate memories, or alternately they can be formed as selected locations in a common physical device. The beamformed signals for a given CPS are stored in the line memories 22 and then weighted and summed in a weighted summer 24. The weighted summer 24 is controlled by a receive amplitude and phase weighting control 26 that provides the weighting values for both amplitude and phase that are used in the weighted summer 24. The weighted summer 24 forms the composite output signal discussed above by weighting the separate beamformed receive signals in any of the ways described above. The memories 22 and the summer 24 can be implemented using analog or digital techniques.

The composite output signal generated by the weighted summer 24 is applied to a display processor 28, which generates display signals that are applied to a display 30. For example, the composite output signals generated by the weighted summer 24 can be used to form conventional B-mode images on the display 30.

In the foregoing example, the composite output signal was formed from a weighted summation of receive signals that had been beamformed. The weighted summation can be performed at baseband, IF or RF. The weighted summation can in alternate embodiments be performed post-detection and even prior to beamforming. Similarly, the weighted summation can be performed either before or after scan conversion.

The foregoing detailed description has discussed only a few of the many forms that this invention can take, and this description is therefore intended by way of illustration, not limitation. It is only the following claims, including all equivalents, that are intended to define the scope of this invention.

What is claimed is:

1. A method of medical diagnostic ultrasound pulsing comprising:

firing a sequence of pulses into a body, where at least two pulses of the sequence have different amplitudes and phase, but no two pulses of the sequence have the same amplitude and opposite phase, and processing the received echoes to reject substantially linear echoes and maintain at least two nonlinear orders, at least one odd order and one even order.

2. The method of claim 1 wherein the sequence of pulses includes at least two pulses, one of which is transmitted at substantially twice the amplitude of the other.

3. The method of claim 2 wherein the sequence of pulses includes at least four pulses, two of which are transmitted at substantially twice the amplitude of the other two.

4. The method of claim 3 wherein the sequence of pulses comprises a first and a second time interleaved series of three pulses.

5. The method of claim 4 wherein each pulse of the second time interleaved series is about 90 degrees out of phase with a corresponding one of the first time interleaved series of pulses.

6. The method of claim 5 wherein the pulse sequence is 1, i, −2, −2i, wherein the coefficients 1 and 2 represent relative amplitudes of the pulses, the minus sign represents a phase shift of the second pulse of about 180 degrees relative to the first pulse in each of the two time interleaved series of pulses, and the i represents a phase shift of about 90 degrees between corresponding pulses of the first and second time interleaves series of pulses.

7. The method of claim 2 wherein the sequence of pulses includes at least three pulses, one of which is transmitted at substantially twice the amplitude of the other two.

8. The method of claim 7 wherein the pulse transmitted at substantially twice the amplitude of the other two pulses is substantially 180 degrees out of phase with the other two pulses.

9. The method of claim 8 wherein the pulse sequence is 1, −2, 1, wherein the coefficients 1, 2, and 1 represent relative amplitudes of the pulses and the minus sign represents a phase shift of the second pulse of about 180° relative to the first pulse.

10. The method of claim 7 wherein the sequence of pulses includes at least six pulses, two of which are transmitted at substantially twice the amplitude of the other four.

11. The method of claim 10 wherein the pulses comprise a first and a second time interleaved series of three pulses.

12. The method of claim 11 wherein each pulse of the second time interleaved series is about 90 degrees out of phase with a corresponding one of the first time interleaved series of pulses.

13. The method of claim 12 wherein the pulse sequence is 1, i, −2, −2i, 1, i, wherein the coefficients 1, 2, and 1 represent relative amplitudes of the pulses, the minus sign represents a phase shift of the second pulse of about 180 degrees relative to the first pulse in each of the two time interleaved series of pulses, and the i represents a phase shift of about 90 degrees between corresponding pulses of the first and second time interleaved series of pulses.

14. The method of claim 1 wherein the pulses of the sequence are all transmitted along a selected scan line.

15. The method of claim 1 wherein the pulses of the sequence comprise a first subset transmitted along a first scan line and a second subset transmitted along a second scan line, spatially distinct from the first scan line.

16. The method of claim 1 wherein at least one of the pulses of the sequence comprises a coded pulse.

17. The method of claim 1 wherein at least one of the pulses of the sequence comprises a chirp-coded pulse.

18. A method of medical ultrasonic processing data comprising:

(a) firing a sequence of pulses into the body, wherein at least two pulses of the sequence have different amplitude and phase from each other;

(b) receiving ultrasound echoes from scatterers in the body in response to each pulse in said sequence;

(c) weighting and summing the received echoes such that only linear echoes from scatterers are significantly suppressed.

19. The method of claim 18 wherein (c) comprises using different receive weights for signals arising from transmitted pulses with equal amplitudes but different phases.

20. The method of claim 18 wherein the pulse sequence of (a) is 0.4, −1, 0.6, −1, wherein coefficients 0.4, 1, and 0.6 represent relative amplitudes of the pulses and the minus sign represents a phase shift of about 180 degrees of the second and fourth pulses in the sequence relative to the first and third pulses in the sequence, and wherein (c) comprises using respective receive weights of 2.5, 3, 5, and 1.

21. The method of claim 18 wherein the pulse sequence of (a) is 0.6, −1, 0.8, −1, wherein coefficients 0.6, 1, and 0.8 represent relative amplitudes of the pulses and the minus sign represents a phase shift of about 180 degrees of the second and fourth pulses in the sequence relative to the first and third pulses in the sequence, and wherein (c) comprises using respective receive weights of 5/3, 3, 3.75, and 1.

22. The method of claim 18 wherein the pulse sequence is 1, +½, −½, −1, wherein coefficients 1 and ½ represent relative amplitudes of the pulses and the minus sign represents a phase shift of about 180 degrees of the third and fourth pulses in the sequence relative to the first and second pulses in the sequence, and wherein (c) comprises using respective receive weights of 3, 8, 24, −5.

23. A method of medical diagnostic ultrasound pulsing comprising:

firing a sequence of pulses into a body along a scan line, where at least two pulses of the sequence have substantially the same amplitude and phase as each other, and at least two pulses of the sequence have different amplitudes from each other, and weighting received echoes responsive to each of the pulses of the sequence with weightings;

wherein a first result of a first multiplication of a first magnitude of a first pulse with a first weight applied to the received echoes responsive to the first pulse is unequal to a second result of a second multiplication of a second magnitude of a second pulse with a second weight applied to the received echoes responsive to the second pulse.

24. The method of claim 23 wherein the at least two pulses that have different amplitudes from each other are also out of phase from each other.

25. The method of claim 24, where the at least two pulses that are out of phase are substantially 180 degrees out of phase with each other.

26. The method of claim 25 wherein the pulse sequence is 1, −2, 1, wherein the coefficients 1, 2, and 1 represent relative amplitudes of the pulses and the minus sign represents a phase shift of the second pulse of about 180° relative to the first pulse.

27. The method of claim 23, further comprising receiving echoes from each of the pulses in the sequence, and weighting and summing the received echoes such that only linear echoes are significantly suppressed.

28. The method of claim 23 where the pulse sequence is 1, 2, 1, wherein the coefficients 1, 2, and 1 represent relative amplitudes of the pulses, and wherein the method further comprises:

(b) receiving ultrasound echoes from scatterers in the body in response to each pulse in said sequence;

(c) weighting the received echoes with a receive weighting of 1, −1, 1; and (d) summing the weighted received echoes.

29. The method of claim 18 wherein the pulses of the sequence are all transmitted along a selected scan line.

30. The method of claim 18 wherein the pulses of the sequence comprise a first subset transmitted along a first scan line and a second subset transmitted along a second scan line, spatially distinct from the first scan line.

31. The method of claim 18 wherein the pulses are transmitted in (a) along a plurality of spatially distinct lines.

32. The method of claim 18 wherein at least one of the pulses of the sequence comprises a coded pulse, and wherein (b) comprises decoding ultrasound echoes received in response to the coded pulse.

33. The method of claim 18 wherein at least one of the pulses of the sequence comprises a chirp-coded pulse, and wherein (b) comprises decoding ultrasound echoes received in response to the chirp-coded pulse.

34. A method of medical diagnostic ultrasound imaging comprising:

(a) selecting
   (i) power levels for transmitting a sequence of ultrasound pulses into a body, and
   (ii) receive weights for applying to echoes received from scatterers in the body, such that the selected transmitted power levels and receive weights preserve echo information from at least second and third order scattering and suppress echo information from first order scattering;

(b) transmitting a sequence of ultrasound pulses into the body at the power levels selected in (a)(i);

(c) receiving echoes from scatterers in the body in response to each pulse in the sequence of pulses;

(d) applying the receive weights selected in (a)(ii) to the received echoes; and (e) displaying an image based on the weighted receive echoes of (d).

35. The method of claim 34 wherein (a) includes placing at least two zeroes in the range of zero velocity plus or minus 30 cm/sec.

36. The method of claim 35 wherein (a) includes placing at least two zeroes at zero velocity.

37. The method of claim 34 wherein the pulses of the sequence are all transmitted along a selected scan line.

38. The method of claim 34 wherein the pulses of the sequence comprise a first subset transmitted along a first scan line and a second subset transmitted along a second scan line, spatially distinct from the first scan line.

39. The method of claim 34 wherein the pulses are transmitted in (b) along a plurality of spatially distinct lines.

40. The method of claim 34 wherein at least one of the pulses of the sequence comprises a coded pulse, and wherein (c) comprises decoding ultrasound echoes received in response to the coded pulse.

41. The method of claim 34 wherein at least one of the pulses of the sequence comprises a chirp-coded pulse, and wherein (c) comprises decoding ultrasound echoes received in response to the chirp-coded pulse.

42. A method of medical diagnostic ultrasound pulsing comprising firing a sequence of pulses into a body, wherein at least two pulses of the sequence differ in amplitude, wherein at least two of the pulses of the sequence differ in phase, and wherein at least a first one of the pulses of the sequence comprises a coded pulse.

43. A method of medical ultrasonic processing comprising firing a sequence of ultrasonic pulses into a body, wherein at least two of the pulses of the sequence differ in phase, wherein at least first and second ones of the pulses are coded with codes of respective lengths, and wherein the first pulse has a larger peak amplitude and a shorter code length than the second pulse.

44. The method of claim 42 or 43 further comprising:

(b) receiving echoes form scatterers in the body in response to each pulse in the sequence of pulses; and (c) combining the received echoes to form a composite output signal in which at least first order echoes are suppressed.

45. The method of claim 44 wherein (b) comprises decoding echoes received in response to each coded pulse.

46. The method of claim 42 or 43 wherein each coded pulse comprises a chirp-coded pulse.

47. The method of claim 42 wherein the sequence of pulses comprises at least a second, uncoded pulse, and wherein the coded pulse is of reduced peak amplitude as compared with the uncoded pulse.

48. The method of claim 42 or 43 wherein the pulses of the sequence are all transmitted along a selected scan line.

49. The method of claim 42 or 43 wherein the pulses of the sequence comprise a first subset transmitted along a first scan line and a second subset transmitted along a second scan line, spatially distinct from the first scan line.

50. The method of claim 42 or 43 wherein the pulses are transmitted along a plurality of spatially distinct lines.

51. A method of medical ultrasonic processing data comprising:

(a) firing a sequence of an even number of pulses into the body, wherein at least two pulses of the sequence differ in phase from each other;

(b) receiving ultrasound echoes from scatterers in the body in response to each pulse in said sequence;

(c) weighting and summing the received echoes such that only linear echoes from scatterers are significantly suppressed;

wherein (c) comprises using different receive weights for signals arising from transmitted pulses having difference phases.

52. A method of medical diagnostic ultrasound processing comprising:

firing a sequence of at least three pulses into a body along a scan line, where at least first and second pulses of the sequence of pulses have substantially the same magnitude and phase as each other, and a third pulse of the sequence of pulses has a different magnitude than the first and second pulses; and weighting first, second and third received echo signals responsive to the first, second and third pulses, respectively, with weights that are substantially the same.

* * * * *